United States Patent
Hu

(10) Patent No.: US 9,061,976 B1
(45) Date of Patent: Jun. 23, 2015

(54) CYCLIC PROCESS FOR THE PRODUCTION OF TAURINE FROM ETHYLENE OXIDE

(71) Applicant: Songzhou Hu, Princeton, NJ (US)

(72) Inventor: Songzhou Hu, Princeton, NJ (US)

(*) Notice: Subject to any disclaimer, the term of this patent is extended or adjusted under 35 U.S.C. 154(b) by 0 days.

(21) Appl. No.: 14/120,491

(22) Filed: May 27, 2014

(51) Int. Cl.
*C07C 309/00* (2006.01)
*C07C 309/14* (2006.01)
*C07C 309/10* (2006.01)

(52) U.S. Cl.
CPC ............ *C07C 309/14* (2013.01); *C07C 309/10* (2013.01)

(58) Field of Classification Search
None
See application file for complete search history.

(56) References Cited

U.S. PATENT DOCUMENTS 8,609,890 B1  12/2013  Hu

OTHER PUBLICATIONS

Database Caplus Chemical Abstracts Service, Columbus, Ohio, US; Database Accession No. 1986:34336, Abstract of Bach et al., DD 219023, Feb. 20, 1985.*
Database Caplus Chemical Abstracts Service, Columbus, Ohio, US; Database Accession No. 1951:46856, Abstract of Vakilwalla et al., Journal of the Indian Chemical Society, Industrial and News Edition (1950), 13, 150-6.*

* cited by examiner

*Primary Examiner* — Karl J Puttlitz

(57) ABSTRACT

The present invention discloses a cyclic process for the production of taurine from ethylene oxide in a high yield of greater than 95% by continuously converting the byproducts of the ammonolysis reaction, sodium ditaurinate and sodium tritaurinate, to sodium taurinate. The cyclic process is completed by using sulfur dioxide or sulfurous acid to neutralize sodium taurinates to recover taurine and to regenerate sodium bisulfite, which is then reacted with ethylene oxide.

10 Claims, 4 Drawing Sheets

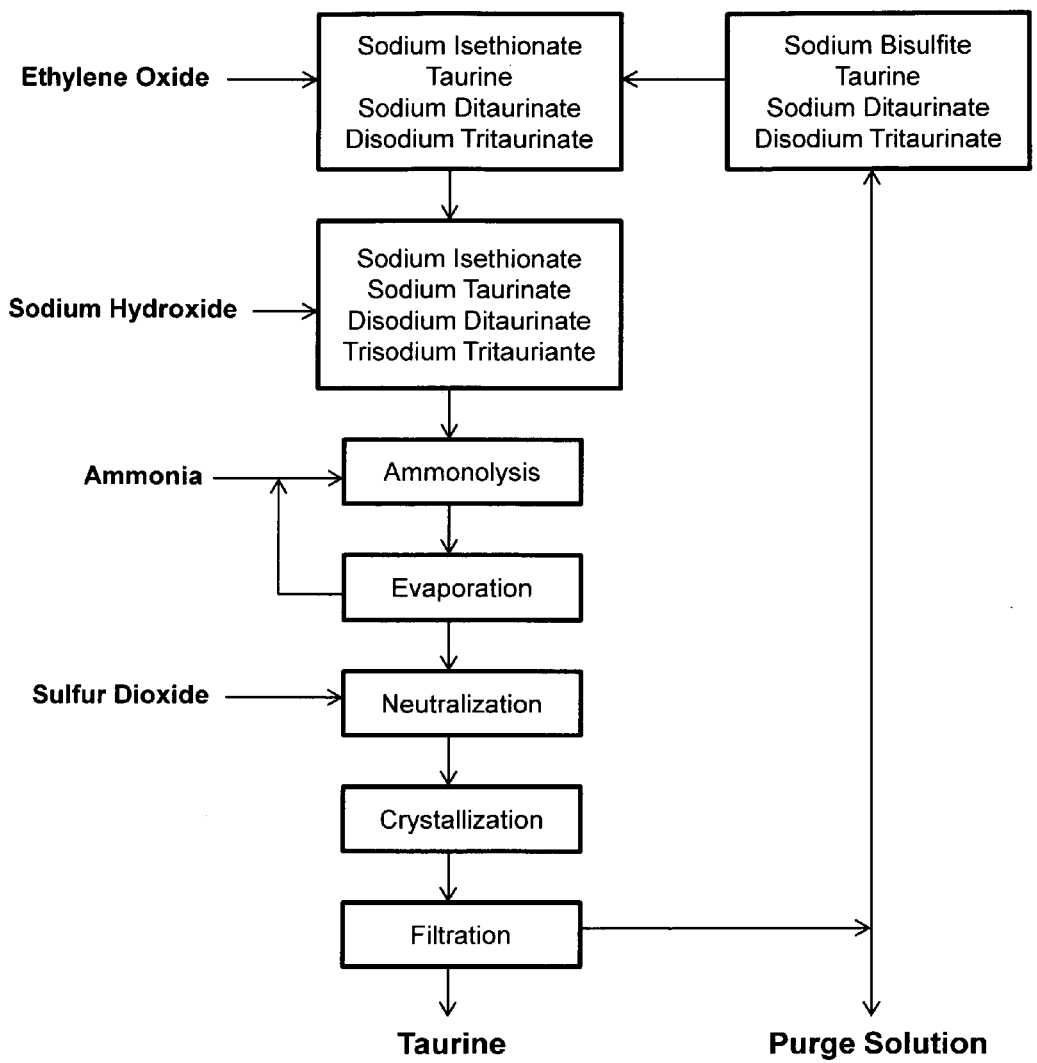
Fig. 1. Schematic Flowchart for the Cyclic Production of Taurine

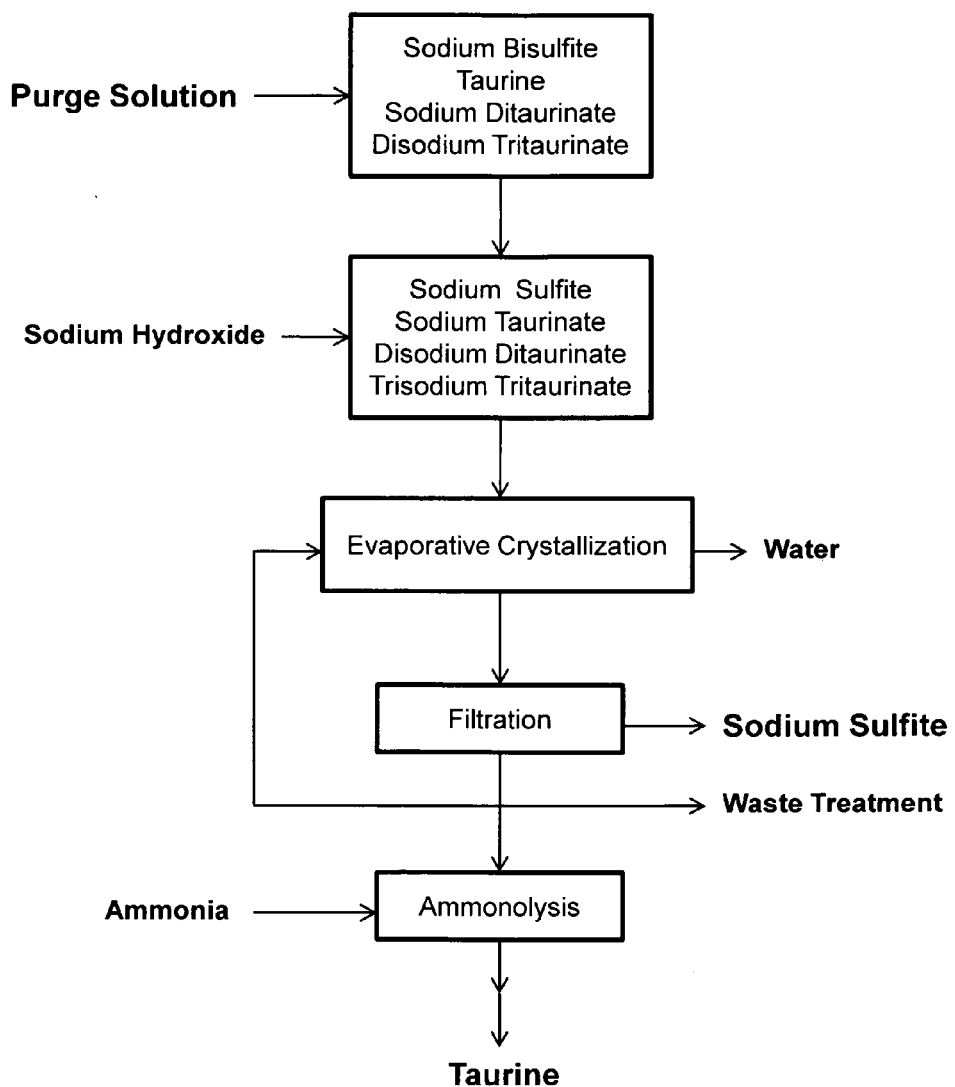
Fig. 2. Schematic Flowchart for the Treatment of Purge Solution

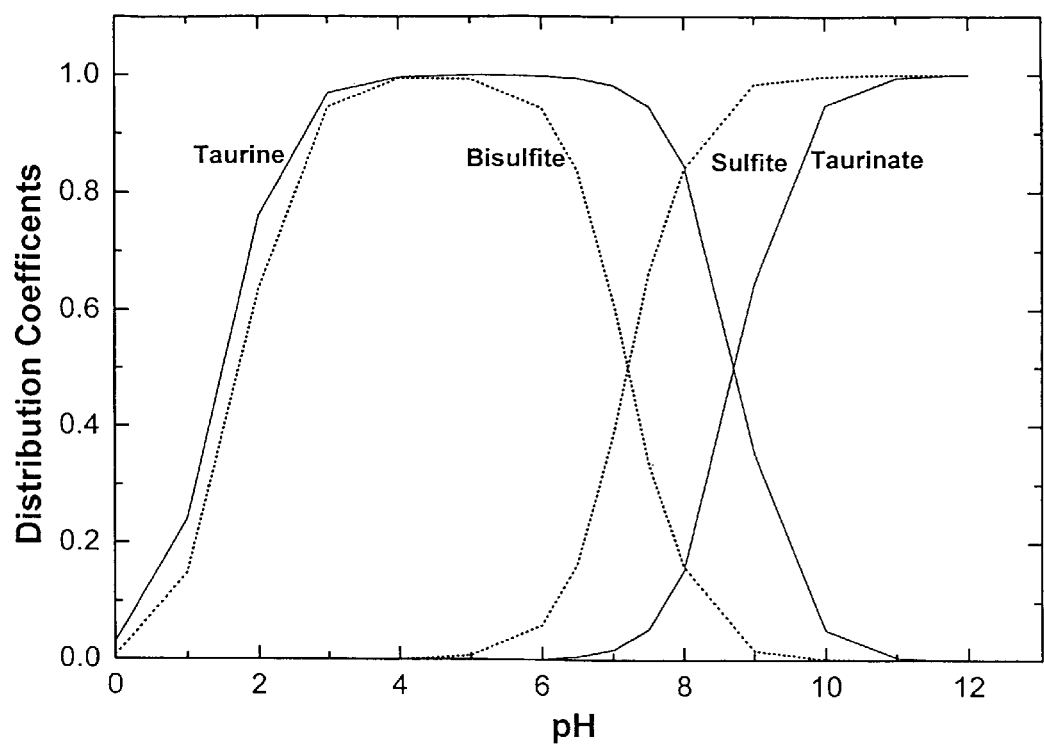
Fig. 3. Distribution of Taurine-Taurinate and Bisulfite-Sulfite

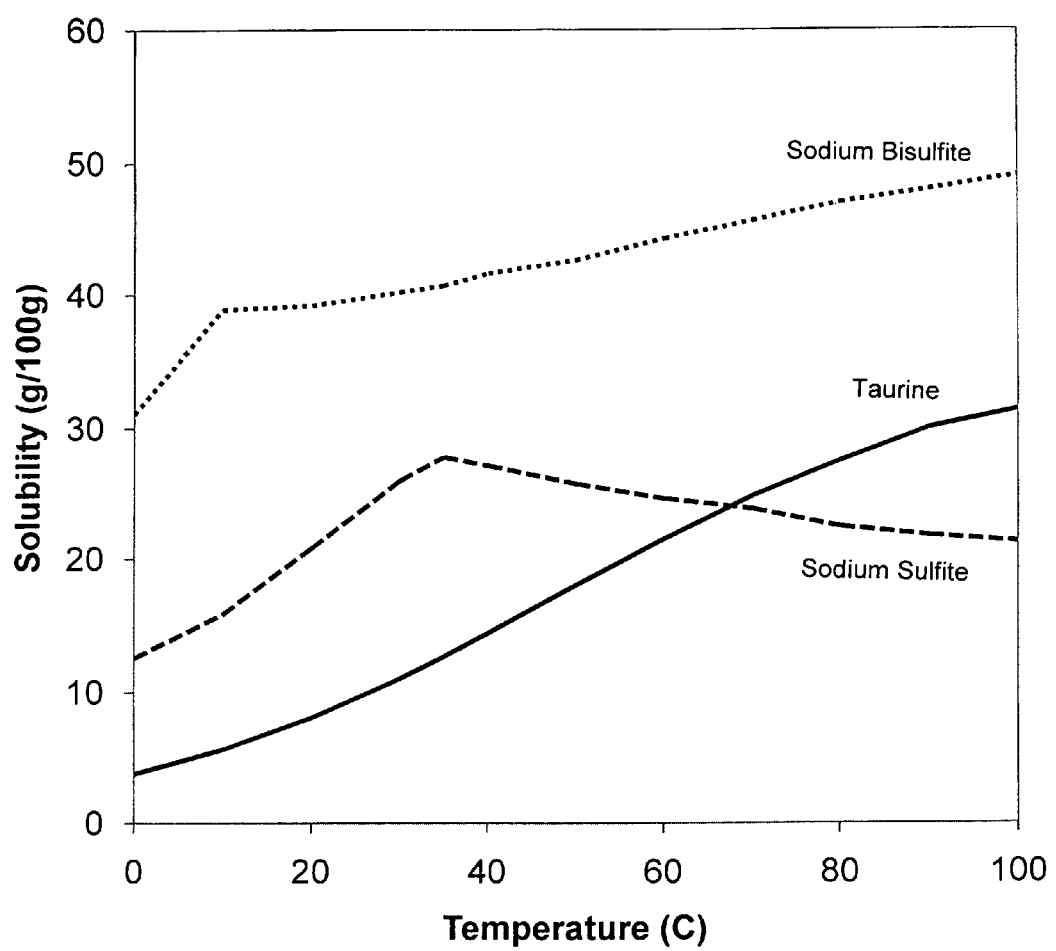
Fig. 4. Solubility of Taurine, Sodium Bisulfite, and Sodium Sulfite

CYCLIC PROCESS FOR THE PRODUCTION OF TAURINE FROM ETHYLENE OXIDE

TECHNICAL FIELD

The present invention relates to a cyclic process for the production of taurine from ethylene oxide in a high overall yield of greater than 95%, by continuously converting the byproducts of the ammonolysis reaction, alkali ditaurinate and alkali tritaurinate, to alkali taurinate and by using sulfur dioxide to generate taurine and to regenerate sodium bisulfite for its reaction with ethylene oxide.

BACKGROUND OF THE INVENTION

Taurine can be referred to as 2-aminoethanesulfonic acid and is one of the amino sulfonic acids found in the tissues of many animals. Taurine is an extremely useful compound because it has such pharmacological effects as detoxification effect, fatigue-relieving effect and nourishing and tonifying effect. As a result, taurine finds wide applications as an essential ingredient for human and animal nutrition.

Taurine is currently produced in an amount of over 50,000 tons per year from ethylene oxide and monoethanolamine. At present time, most of the taurine is produced from ethylene oxide, following a three-step process: (1) the addition reaction of ethylene oxide with sodium bisulfite to yield sodium isethionate; (2) ammonolysis of sodium isethionate to yield sodium taurinate; (3) neutralization with an acid, i.e., hydrochloric acid and, preferably, sulfuric acid, to generate taurine and sodium sulfate.

Although the ethylene oxide process is well established and widely practiced in industrial production, the overall yield is not very high, less than 80%. Moreover, the process generates a large amount of waste stream and sodium sulfate which is of little value and increasingly difficult to dispose of.

U.S. Pat. No. 8,609,890, incorporated herein by reference, discloses a cyclic process for the production of taurine in which sulfuric acid in the neutralization stage is replaced with sulfur dioxide or sulfurous acid. This cyclic process overcomes some of the disadvantages of the known ethylene oxide process by regenerating sodium bisulfite for its reuse in the addition reaction with ethylene oxide, thus eliminating the formation of large quantity of sodium sulfate as by product.

When the cyclic process is used in accordance with U.S. Pat. No. 8,609,890 for several cycles, impurities are found to accumulate to the extent that a new cycle has to be started. The overall yield for the cyclic process is still less than 85%.

It is an object of the present invention to overcome the disadvantage of the cyclic process in U.S. Pat. No. 8,609,890 for the production of taurine from ethylene oxide. The improved cyclic process can be carried out indefinitely and the overall yield is increased to greater than 90%, in particular, to 95%, and to nearly quantitative. This high yield is achieved by continuously converting the impurities, now identified as sodium ditaurinate and sodium tritaurinate, to sodium taurinate in the ethylene oxide process.

It is another object of the present invention to disclose a process for the effective separation of excess sodium sulfite from taurine, sodium ditaurinate, and sodium tritaurinate in the purge solution. Sodium ditaurinate, sodium tritaurinate, and unreacted sodium isethionate, present in the purge solution, are then converted to sodium taurinate.

DESCRIPTION OF THE DRAWINGS

FIG. 1. Schematic flowchart for the cyclic production of taurine from ethylene oxide.

FIG. 2. Schematic flowchart for the treatment of the purge solution and the evaporative crystallization and separation of excess sodium sulfite.

FIG. 3. Distribution of taurine and sodium sulfite at different pH.

FIG. 4. Solubility curve of taurine, sodium bisulfite, and sodium sulfite.

DESCRIPTION OF THE INVENTION

The present invention relates to a cyclic process for the production of taurine from ethylene oxide in a high yield, i.e., greater than 90%, in particular, greater than 95% to nearly quantitative. The cyclic process is schematically illustrated in FIG. 1 and the reactions are described as follows:

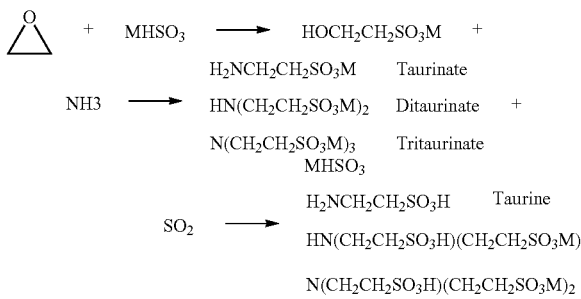

In the reaction scheme, M stands for alkali metals, i.e., lithium, sodium, potassium, and cesium. Sodium is most preferably used in the production of taurine and in the following description of the process, only sodium is used, but other alkali metals are equally useful.

The process according to the present invention starts with the addition of ethylene oxide with sodium bisulfite to yield sodium isethionate in the presence of taurine, sodium ditaurinate, and sodium tritaurinate, which are present in the mother liquor from the production of taurine.

The addition reaction of ethylene oxide with sodium bisulfite is carried out in a range of pH 4 to 10, preferably pH 4 to 8, and most preferably pH 4.5 to 6, because in this range of pH, sulfite is present as bisulfite as shown in FIG. 3. The reaction temperature is maintained at 20 to 80° C., preferably 40 to 50° C. The reaction can be carried out at normal pressure, increased pressure, or reduced pressure.

The molar ratio of ethylene oxide to sodium bisulfite is in the range of 0.8 to 1.1, in particular, in the range of 0.9 to 0.98. The presence of a slight excess of sodium bisulfite and sodium sulfite is beneficial to inhibit the reaction of ethylene oxide with taurine and sodium ditaurinate. It has been found that ethylene oxide reacts selectively with sodium bisulfite to yield sodium isethionate even in the presence of taurine and sodium ditaurinate.

To the solution of a mixture of sodium isethionate, sodium ditaurinate, and tritaurinate, is added a solution of inorganic base, which can be alkali hydroxide or alkali carbonate. The most preferable base is sodium hydroxide. The amount of sodium hydroxide can be from 1 to 20%, preferably 3 to 8%, of the total molar amount of sodium isethionate in the reaction system. The amount of sodium hydroxide used is sufficient to convert excess sodium bisulfite into sodium sulfite, taurine into sodium taurinate, sodium ditaurinate into disodium ditaurinate. Excess amount of sodium hydroxide can be used, but no advantage is gained for the ammonolysis reaction.

The use of alkali hydroxide or alkali carbonate is essential for the ammonolysis of sodium isethionate and for the ammonolysis reaction to reach the equilibrium state. Otherwise, sodium ditaurinate and sodium tritaurinate will accumulate in the reaction system. This novel finding ensures that the cyclic process can be carried out indefinitely and the yield for the cyclic process is very high, i.e., greater than 90%, in particular 95% to nearly quantitative.

The concentration of solid mass in a solution of sodium isethionate and sodium taurinates can be varied from 5% to 30%, preferably adjusted to a range of 20 to 25%. Then the solution is saturated with ammonia. The molar ratio of ammonia, relative to the total molar amount of sodium isethionate and sodium taurinates can be from 5 to 25, preferably maintained from 8 to 10. At higher molar ratio, the equilibrium is shifted to the formation to sodium taurinate at the costly expense of recovering excess ammonia. At lower molar ratio, the formation of sodium ditaurinate and sodium tritaurinate is excessive.

The ammonolysis is usually carried out at a temperature from 180° C. to 260° C. under the pressure from autogenous to 260 bars for 1 to 6 hours, optionally in the presence of catalysts. Useful catalysts are the alkaline salts of sodium, potassium and lithium. Such salts are sodium hydroxide, potassium hydroxide, lithium hydroxide, sodium carbonate, potassium carbonate, lithium carbonate, sodium sulfate, sodium sulfite, potassium sulfate, potassium sulfite. Catalysts exogenous to the reaction systems can be used, but catalysts inherently present in the cyclic process are preferred, in particular, a combination of sodium sulfite and sodium hydroxide is found to be very effective for the ammonolysis reaction.

After the ammonolysis reaction, excess ammonia are dispelled from the reaction solution and reclaimed for reuse. Sodium taurinate is obtained, along with sodium ditaurinate, sodium tritaurinate, and unreacted sodium isethionate.

The alkaline solution of sodium taurinates is neutralized with sulfur dioxide or sulfurous acid to pH 3 to 8, preferably pH 4.5-5.5, to yield taurine and to regenerate sodium bisulfite. Taurine is separated from the cooled crystalline suspension by filtration. Crude taurine is refined to pharmaceutical grade by one or more recrystallization from deionized water.

The mother liquor, after the separation of taurine, contains the regenerated sodium bisulfite, residual taurine, sodium ditaurinate, sodium tritaurinate, and a small amount of unreacted sodium isethionate. However, the amount of sodium bisulfite in the mother liquor is in excess for its reaction with ethylene oxide to complete the cycle, because extra amount of sulfur dioxide is needed to neutralize the sodium hydroxide introduced into the system. Therefore, some of the mother liquor is taken out from the cyclic process as purge solution. This bleeding process, essential for an indefinitely cyclic process, has the benefits of removing other impurities, such as sodium sulfate from the oxidation of sodium bisulfite and glycol from the reaction of ethylene oxide with water, from the cyclic process.

The amount of the purge solution is from 1 to 15%, preferably 3 to 8%, of the total volume, depending on the amount of sodium hydroxide. Usually, the molar amount of sodium bisulfite, purged from mother liquor, is nearly the same as the molar amount of sodium hydroxide introduced into the cyclic process.

To recover the value of residual taurine, sodium ditaurinate, and sodium tritaurinate from the otherwise waste stream, the purge solution at a pH of 4.5 to 5.5, is reacted with a solution of sodium hydroxide to a pH of 9.5 to 12, preferably to a pH of 10 to 11. As can be seen from FIG. 3, sulfite is present mainly as sodium sulfite, while taurine is converted to sodium taurinate at this alkaline pH of greater than 10. A particular advantage for adjusting pH is that the very soluble sodium bisulfate is turned to much less soluble sodium sulfite, while the barely soluble taurine is changed to a highly soluble form of sodium taurinate. The solubility of sodium taurinate is determined to be 86 g/100 g at room temperature. In FIG. 4, the reversal of the solubility of sodium bisulfate-sodium sulfite and taurine-sodium taurinate as the pH changes from acidic to basic is clearly illustrated. The separation of sodium sulfite from sodium taurinate, sodium ditaurinate, and sodium tritaurinate, is achieved by an evaporative crystallization as described in FIG. 2.

After sodium sulfite is removed from the suspension, the mother liquor is consisted of mainly sodium ditaurinate, residual sodium taurinate, sodium tritaurinate, and sodium isethionate. The mother liquor is then saturated with ammonia and returned to the ammonolysis stage in the cyclic process or subjected to the ammonolysis reaction to yield sodium taurinate.

The process according to the present invention can be carried out discontinuously, semi-continuously, and continuously.

It should be appreciated that the cyclic process according to the present invention allows the production of taurine from ethylene oxide in high yield, i.e., from 90% to nearly quantitative, and generates no waste other than a small amount of sodium sulfite, which by itself is a valuable commodity.

The following examples will illustrate the practice of this invention but are not intended to limit its scope.

EXAMPLE 1

To 500 mL solution of the mother liquor, consisting of 1.05 mole of regenerated sodium bisulfite and 0.14 mole of taurinates (including taurine, sodium ditaurinate, and sodium tritaurinate), is added 44 g of ethylene oxide (1.0 mole) at 40-50° C. to form a solution of sodium isethionate, followed by addition of 180 g of gaseous ammonia and 15 g of 30% sodium hydroxide. The solution is placed in an autoclave and heated to 260° C. for 2 hours under autogenous pressure. After removal of ammonia, sulfur dioxide is blowing in to pH 4.5 to obtain a crystalline suspension of taurine. After filtration to obtain the first batch of taurine, the mother liquor is concentrated and cooled to obtain a second batch of taurine for a total of 119 g in a yield of 95%.

EXAMPLE 2

To 600 mL of the purge solution, same as the mother liquor after filtering off the taurine, is added enough sodium hydroxide to a pH of 11. The solution is concentrated at 70-80° C. under reduced pressure to obtain a crystalline suspension of sodium sulfite, which is removed by filtration. The mother liquor is repeatedly concentrated so that the concentration of residual sodium taurinates (including sodium taurinate, sodium ditaurinate, and sodium tritaurinate) reaches to about 25% in the solution. The solution is then saturated with ammonia and returned to the ammonolysis stage in Example 1.

It will be understood that the foregoing examples, explanation, drawings are for illustrative purposes only and that in view of the instant disclosure various modifications of the present invention will be self-evident to those skilled in the art and are to be included within the spirit and purview of this application and the scope of the appended claims.

What is claimed is:

1. A cyclic process for the production of taurine from ethylene oxide in high yield, comprising,
   (a) Reacting ethylene oxide with sodium bisulfite in the presence of taurine, sodium ditaurinate, and sodium tritaurinate, to yield a mixture of sodium isethionate and sodium taurinates;
   (b) Adding sodium hydroxide to (a) to convert excess sodium bisulfite to sodium sulfite, taurines to sodium taurinates;
   (c) Adding ammonia to (b) and subjecting the solution to the ammonolysis reaction to yield a mixture of sodium taurinates in the presence of catalysts;
   (d) Removing excess ammonia from (c) and neutralizing sodium taurinates with sulfur dioxide or sulfurous acid to form a crystalline suspension of taurine in a solution of sodium ditaurinate, sodium tritaurinate, and sodium bisulfite;
   (e) Recovering taurine from (d), and returning most of the mother liquor to (a) to react with ethylene oxide.

2. The process according to claim 1 wherein the overall yield is from greater than 90%.

3. The process according to claim 1(b) wherein the amount of sodium hydroxide is from 1 to 25% of sodium isethionate.

4. The process according to claim 1(c) wherein the molar ratio of ammonia to sodium isethionate is from 5 to 15.

5. The process according to claim 1(c) wherein the catalysts are alkali hydroxide and alkali carbonate.

6. The process according to claim 1(e) wherein part of the mother liquor is taken out from the cyclic process and adjusted to pH 9 to 12 with sodium hydroxide to form sodium sulfite and sodium taurinates.

7. The process according to claim 6 wherein sodium sulfite is separated from sodium taurinates by evaporative crystallization and cooling crystallization.

8. The process according to claim 7 wherein the mother liquor after filtration of sodium sulfite is saturated with ammonia and returned to the ammonolysis step or subjected to the ammonolysis reaction to yield a mixture of sodium taurinates.

9. The process according to claim 2, wherein the overall yield is greater than 95%, to nearly quantitative.

10. The process according to claim 5, wherein the catalysts are a combination of sodium sulfite and sodium hydroxide.

* * * * *